US011366107B2

(12) United States Patent
Hegedüs et al.

(10) Patent No.: US 11,366,107 B2
(45) Date of Patent: Jun. 21, 2022

(54) IMMUNOASSAY FOR WHOLE BLOOD SAMPLES

(71) Applicant: Diatron MI PLC, Budapest (HU)

(72) Inventors: Márton Hegedüs, Budapest (HU); Dimitris Giantzoudis, Herts (GB)

(73) Assignee: DIATRON MI PLC, Budapest (HU)

( * ) Notice: Subject to any disclaimer, the term of this patent is extended or adjusted under 35 U.S.C. 154(b) by 2 days.

(21) Appl. No.: 16/412,141

(22) Filed: May 14, 2019

(65) Prior Publication Data

US 2019/0346441 A1 Nov. 14, 2019

(30) Foreign Application Priority Data

May 14, 2018 (LU) ........................................ 100795

(51) Int. Cl.
*G01N 33/536* (2006.01)
*G01N 21/27* (2006.01)
*G01N 21/31* (2006.01)

(52) U.S. Cl.
CPC ......... *G01N 33/536* (2013.01); *G01N 21/272* (2013.01); *G01N 21/31* (2013.01); *G01N 2333/4737* (2013.01)

(58) Field of Classification Search
CPC ............. G01N 21/82; G01N 2021/825; G01N 33/536; G01N 33/537; G01N 21/272; G01N 21/31; G01N 2333/4737; G01N 33/5302; A61B 5/150755
USPC .............................. 436/66, 71, 536; 435/7.92
See application file for complete search history.

(56) References Cited

U.S. PATENT DOCUMENTS

| | | | | |
|---|---|---|---|---|
| 4,637,978 A * | 1/1987 | Dappen | ................ | G01N 33/526 422/400 |
| 5,284,940 A * | 2/1994 | Lin | ........................ | C07K 16/44 435/270 |
| 5,674,699 A * | 10/1997 | Saunders | ......... | G01N 33/54313 435/7.1 |
| 6,030,845 A | 2/2000 | Yamao et al. | | |
| 6,060,598 A * | 5/2000 | Devlin | ................ | A61K 49/0015 436/172 |
| 6,090,568 A * | 7/2000 | Belly | ............... | G01N 33/54386 435/7.92 |
| 6,716,642 B1 * | 4/2004 | Wu | ...................... | B01J 19/0046 250/338.2 |
| 6,855,562 B1 * | 2/2005 | Yamao | .................. | G01N 21/82 356/39 |
| 2002/0031791 A1 * | 3/2002 | Uchida | ................ | G01N 33/53 435/7.21 |
| 2002/0123154 A1 * | 9/2002 | Burshteyn | ............ | B01D 61/147 436/177 |
| 2003/0027341 A1 * | 2/2003 | Samsoondar | .......... | G01N 33/96 436/22 |
| 2003/0059766 A1 * | 3/2003 | Goertz | ............... | G01N 33/5432 435/5 |
| 2004/0121417 A1 * | 6/2004 | Kamei | ................. | G01N 33/542 435/7.92 |
| 2005/0051466 A1 * | 3/2005 | Carter | .................. | G01N 15/042 210/512.1 |
| 2007/0215467 A1 * | 9/2007 | Soma | ................... | G01N 35/025 204/416 |
| 2009/0047690 A1 * | 2/2009 | Goldberg | ......... | G01N 33/56972 435/7.24 |
| 2010/0075338 A1 | 3/2010 | Vessey et al. | | |
| 2010/0086930 A1 * | 4/2010 | Soukka | ................ | G01N 33/542 435/6.16 |
| 2010/0183721 A1 * | 7/2010 | Williams | ............. | A61K 9/5161 424/484 |
| 2012/0009581 A1 * | 1/2012 | Bankaitis-Davis | ........................ | G01N 33/57434 435/6.12 |
| 2012/0142032 A1 * | 6/2012 | Morgan | ........... | G01N 33/56972 435/7.24 |
| 2014/0034177 A1 | 2/2014 | Bentley | | |
| 2014/0273070 A1 * | 9/2014 | Hale | ....................... | G01N 1/40 435/30 |

(Continued)

FOREIGN PATENT DOCUMENTS

| | | |
|---|---|---|
| CN | 105334333 A | 2/2016 |
| EP | 0822412 B1 | 9/2005 |

(Continued)

OTHER PUBLICATIONS

Zelmanovic, D., Garcia, R.A. and Turrell, J, Automated Instrumentation, Hematology, Kirk-Othmer Encyclopedia of Chemical Technology, Ed., (2000), 1-13 (Year: 2000).*

*Primary Examiner* — Ann Montgomery
(74) *Attorney, Agent, or Firm* — 24IP Law Group USA, PLLC; Timothy Dewitt

(57) ABSTRACT

The present invention describes a method of performing immunoassay measurements on whole blood samples for biomarker quantification. These tests are routinely performed on serum or plasma separated from whole blood samples. Prior art also involves application of complex multi-component assays or methods using insoluble particles for these measurements. A solution capable of working on whole blood samples, offering advantages in assay simplicity, cost-effectiveness and shortened measurement times was desired. The present invention solves these issues using simple immunoturbidimetry for whole blood samples without relying on particle enhancement of the reaction. To achieve this goal the agglutination reaction between antibodies and antigens is performed, measured and evaluated according to the disclosed method for whole blood assays.

11 Claims, 2 Drawing Sheets

(56) References Cited

U.S. PATENT DOCUMENTS

| | | | |
|---|---|---|---|
| 2014/0302526 A1* | 10/2014 | Tang | G01N 33/57426 435/7.4 |
| 2015/0044780 A1 | 2/2015 | Kurtz et al. | |
| 2017/0080104 A1* | 3/2017 | Irvine | A61K 47/6889 |
| 2019/0292235 A1* | 9/2019 | Maglia | G01N 33/48721 |
| 2020/0316599 A1* | 10/2020 | Shi | G01N 15/06 |

FOREIGN PATENT DOCUMENTS

| | | |
|---|---|---|
| EP | 2804005 A1 | 11/2014 |
| EP | 2135075 B1 | 10/2016 |
| WO | 20080114060 A1 | 9/2008 |
| WO | 2016000216 A1 | 1/2016 |

\* cited by examiner

IMMUNOASSAY FOR WHOLE BLOOD SAMPLES

CROSS-REFERENCE TO RELATED APPLICATIONS

The present application claims priority to Luxembourg Patent Application No. LU 100795 filed on May 14, 2018. The aforementioned application is hereby incorporated by reference in its entirety.

BACKGROUND OF THE INVENTION

Filed of the Invention

The invention relates to an immunoassay for whole blood samples.

Brief Description of the Related Art

Biomarker detection and quantification in biological samples relies on different methods, depending on the type of analyte or sample and desired assay performance. Immunoturbidimetry is a routinely used method in the field of clinical chemistry. It is primarily used for the quantitative detection of specific proteins (e.g. C-reactive protein (CRP), D-dimer, HbA1c, Immunoglobulins, Transferrin, etc.).

Immunoturbidimetry is a homogenous, label-free and therefore simple immunoassay method, which measures the change in optical absorbance of the reaction mixture at specific wavelengths. An alternative assay method, immunonephelometry measures the change in light scattering instead of absorbance. Both methods take advantage of the specific binding of antibodies directed against targeted molecules. This complex formation results in an agglutination reaction which is reflected by a turbidity change of the mixture. Concentration dependent turbidity change is then compared to that produced by standards with known analyte concentrations.

Conventional immunoturbidimetry reagents consist of a reaction buffer and a solution of antibodies. Under optimized conditions the antibodies form a three-dimensional lattice with antigens in the sample to be analyzed. As a more advanced method, particle enhancement of the agglutination reaction was developed later. This usually involves the application of latex beads on the surface of which the antibodies are adsorbed to give a stronger signal. Besides the most widely used latex beads, application of other non-soluble particles is also known (e.g. colloidal gold).

The optimization of conventional immunoturbidimetry for serum (eventually plasma) and urine as samples is known in the prior art. These assays suffer from interference with higher amounts of blood cells and/or cellular components (e.g. erythrocytes, hemoglobin). Using simple immunoturbidimetry for measurement of blood biomarkers therefore required dedicated serum or plasma samples.

Direct measurement of whole blood samples with immunoturbidimetry was only possible using particle enhancement techniques, most commonly latex immunoturbidimetry, after hemolysis of the blood sample. Different companies have been using this solution for the measurement of e.g. CRP on blood samples in stand-alone analyzers or in combination with hematological analysis (Mindray: WO2016/000216 A1, CN 105334333A, Quotient: US 2010075338 A1, EP 2 135 075 B1, Horiba: U.S. Pat. No. 6,030,845, EP 0 822 412 B1).

Published International patent application WO 2008/114060 A1 relates to a method and apparatus to estimate the concentration of a target substance (e.g. cholesterol or CRP) in the plasma component of a whole blood sample without the need to separate the red blood cells from the plasma prior to testing, thereby simplifying the design and construction of the test device. According to this publication, the analyte under investigation is measured in a time dependent (bio-/immuno-) chemical reaction and measured separately, a marker substance (e.g. haemoglobin) for the estimation of red blood cell volume, using a non-time-dependent alteration in physical property of the reaction mixture (in this instance, transmission) attributed to inherent filter effects on sample addition. These non-time-dependent changes are not part of the reaction chemistry and are resolved from the time dependent alteration in physical property caused by the assay chemistry by continuous measurement and mathematical modelling. Algorithms that combine these two parameters are used to estimate the target substance and compensate for variations in the percentage haematocrit of the sample. The method equalises the assay response for subtle variations in patient sample (e.g. haematocrit).

The routinely used serum or plasma separation from whole blood samples is associated with drawbacks including inconvenience for patients and staff due to additional sample collection (especially for pediatric or geriatric cases), time, cost, instrumentation and labor expenses associated with serum/plasma separation by e.g. filtration or centrifugation.

Known alternatives to conventional immunoturbidimetry are also dominantly optimized for serum or plasma samples, and they involve more sophisticated methods, e.g.: ELISA (Enzyme-Linked Immuno-Sorbent Assay), FPIA (Fluorescence Polarization ImmunoAssay), QCM (Quartz Cristal Microbalance), OWLS (Optical Waveguide Lightmode Spectroscopy), conjugated magnetic particles, electrochemical immunosensors. These methods may involve more complex assay systems with special reagents, multiple reaction steps, interaction between a solid carrier surface and the liquid phase, application of different labels or reporting molecules (e.g. enzymatic, fluorescent, electrochemiluminescent). These methods offer advantages, but a disadvantage is the need for complex instrumentation which is associated with high assay complexity and often prolonged measurement times.

Most immunoassays in routine use, including many variants of prior art immunoturbidimetry, are designed for special analysis instruments of clinical chemistry laboratories. Requirements of a laboratory application may differ in many aspects from requirements of a near-patient or point-of-care (PoC) setting. For the high number of samples in high throughput laboratories the number of performed tests per hour is in focus, with assay and instrumentation complexity being of less concern. Simultaneous parallel processing of numerous samples in these laboratories reduces the importance of the duration of individual tests. This is possible because high throughput can be achieved on the longer term by running a high number of assays simultaneously, even if each of these assays needs a longer time for execution. In contrast to this, the simplicity of the system or measurement device, as well as single test time in serial sample processing are of major importance in a PoC scenario.

Medical practice often does not evaluate single laboratory parameters, but commonly a set of different biomarkers. Blood cell analysis provides basic background information as well as specific diagnostic results in certain cases. Whole blood samples are needed for automated blood cell counting, but many other biologically relevant parameters require additional serum samples for analysis. The use of a single sample for blood cell counting and determination of additional biomarkers is desired to simplify diagnostic procedures. From a technical aspect, easy integration of the immunoturbidimetry measurement with other parts of a device at a system level is an important step for an integrated solution.

Immunoassay methods using latex beads or other insoluble particles for immunoassay measurements on whole blood samples have created an intricate IP situation (Mindray: WO2016/000216 A1, CN 105334333A, Quotient: US 2010075338 A1, EP 2 135 075 B1, Horiba: U.S. Pat. No. 6,030,845, EP 0 822 412 B1). It is a disadvantage that particle enhanced reagents require additional compounds and manufacturing steps (e.g. latex beads or other non-soluble particles, binding of antibodies to the particle surface) during production, with associated complexity and costs. Some technical problems, like spontaneous agglutination and settling of particles, or particle adhesion to the surface of the measurement cell (Horiba: US 2014/0341779 A1, EP 2 804 005 A1) make dedicated countermeasures necessary in case of particle enhanced methods.

SUMMARY OF THE INVENTION

It is an object of the present invention to provide materials and a method for an immunoassay method which works on whole blood samples without particle enhancement.

The present disclosure provides a method for measuring an immunoreaction, the method comprising the steps of:
a. Providing a whole blood sample;
b. Adding a reaction buffer comprising a non-ionic detergent for hemolysis;
c. Incubating the mixture of steps a. and b. in a temperature range between 22° to 28° C.;
d. Adding to the mixture a buffered solution, which is free of any insoluble antibody carrier, comprising at least one specific antibody binding at least one specific target;
e. Incubating the mixture of step d. in a temperature range between 22° to 28° C.; and
f. Measuring the change in absorbance or in scattered light of the mixture during incubation at a wavelength in a range between 600 nm to 680 nm.

In a further aspect of the invention the incubation temperature may be in a range between 24° C. to 26° C. and the absorbance may be determined in a range between 620 nm to 650 nm.

The method may further comprise as an additional step applying adaptive signal evaluation dominated by fixed-point calculation for low signal samples and by end-point calculation for high signal samples.

It is envisaged that the concentration of the non-ionic detergent shall be above 0.5% (w/v).

The final reaction mixture comprising the at least one antibody may comprise whole blood sample in a concentration of at least 10% (v/v).

It is envisaged in a further embodiment, that the absorbance has been determined at least at two points in time prior to adding the buffered solution comprising the at least one antibody to ensure completeness of hemolysis and absence of artifacts by detecting a constant absorbance.

In a further aspect of the invention, the method may comprise the step of determining the absorbance at least once after adding the buffered solution comprising the at least one antibody.

It is further envisaged that the absorbance may be determined shortly after addition of the at least one antibody and at a second time at the end of total incubation.

The method may further comprise determination of values for cell counting.

It may also be part of the present method to determine the hematocrit.

The method may further encompass multiple readings or real-time determination of absorbance.

Another object of the present invention is the use of the described method for measuring an immunoreaction.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

The invention will now be described on the basis of figures. It will be understood that the embodiments and aspects of the invention described in the figures are only examples and do not limit the protective scope of the claims in any way. The invention is defined by the claims and their equivalents. It will be understood that features of one aspect or embodiment of the invention can be combined with a feature of a different aspect or aspects of other embodiments of the invention, in which:

DETAILED DESCRIPTION OF THE INVENTION

Figure 1:
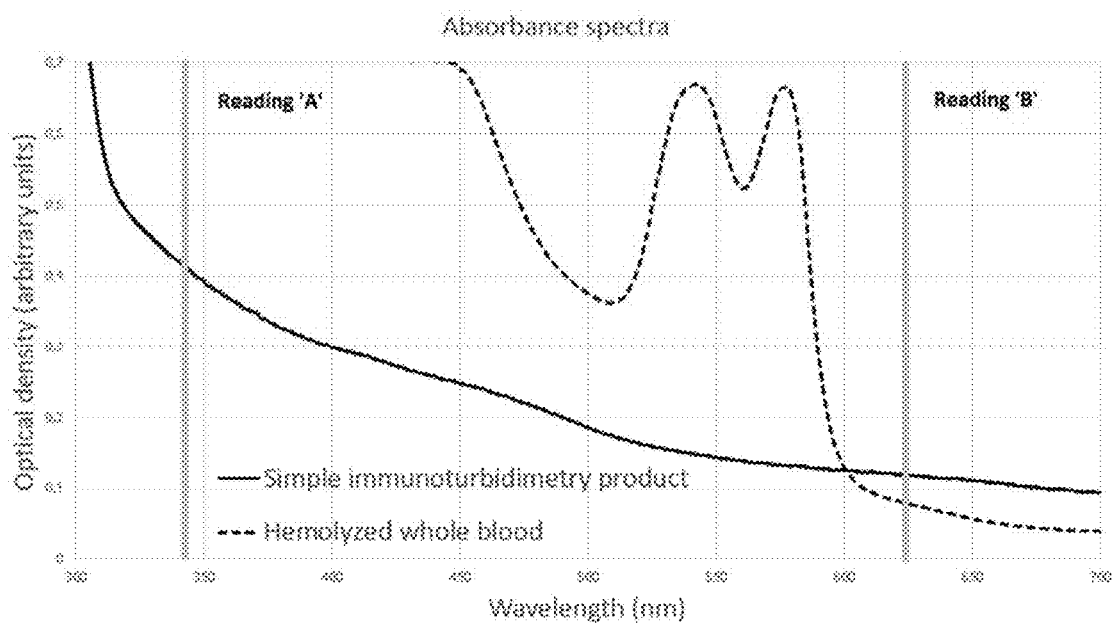
FIG. 1 shows absorption spectra in the 300-700 nm wavelength range.

The technical problem is solved by the independent claims. The dependent claims cover further specific embodiments of the invention.

The present invention describes a method of performing immunoassay measurements on whole blood samples for biomarker quantification. These tests are routinely performed on serum or plasma separated from whole blood samples. Prior art also involves application of complex multi-component assays or methods using insoluble particles for these measurements. A solution capable of working on whole blood samples, offering advantages in assay simplicity, cost-effectiveness and shortened measurement times was desired. The present invention solves these issues using simple immunoturbidimetry for whole blood samples without relying on particle enhancement of the reaction. To achieve this goal the agglutination reaction between antibodies and antigens is performed, measured and evaluated according to the disclosed method for whole blood assays.

A buffered solution comprising insoluble antibody carriers designates solutions used in particle enhancement techniques, most commonly latex immunoturbidimetry. Such solutions are used in the prior art after hemolysis of the blood sample as described above. The high number of antibodies bound together to such carriers or particles and the increased size (thus light scattering) of antigen-antibody aggregates plays a pivotal role in the increased sensitivity of insoluble antibody carrier enhanced assays. The present invention provides a method for whole blood samples which is free of such carriers.

The present invention is based on extensive experimental research and development for finding a solution that avoids problems associated with prior art methods. The result is the claimed new solution allowing simple immunoturbidimetry measurements of blood samples. The new method is based on the use of a buffered solution of simple antibodies, without non-soluble particles as an active ingredient for assays on blood samples. Thus, a single whole blood sample can be used for both blood cell counting and determination of one or more further biomarkers using immunoturbidimetry without particle enhancement.

The claimed immunoassay method works on whole blood samples without particle enhancement. It relies on the measurement of a change in absorbance or in scattered light of the reaction solution; using a high sample ratio, and hemolysis with reduced interference with the immunoturbidimetry reaction. The optical measurement is performed at a wavelength in a sub-optimal range for immunoturbidimetry and with significant parallel hemoglobin absorption. Measurement artifacts under these circumstances are alleviated by reduced reaction temperature optimized for whole blood samples and adaptive signal calculation based on signal amplitude.

The input sample for the described immunoassay method can be whole blood, partially or fully separated plasma or serum or other body fluids. Conventional immunoturbidimetry with simple antibodies is routinely optimized for serum or plasma, but the presence of cells in the sample produces an extreme turbidity which makes optical measurements impossible. Only high sample dilution can reduce this interference but in parallel it also reduces analyte concentration to an undetectable level. As a well-known solution to reduce turbidity, cells can be hemolyzed physically (e.g. freezing, ultrasonication) or using chemical reagents.

After hemolysis, hemoglobin is released from erythrocytes in extreme amounts. Due to its high absorbance in a wide wavelength range hemoglobin interferes with conventional immunoturbidimetry measurements. Accurate photometric measurements are only possible if there is no considerable interference originating from background absorption of the solution. As hemoglobin absorbs very strongly below 600 nm, significantly limiting the penetration of light, a longer measurement wavelength has to be chosen. Particle enhancement immunoturbidimetry methods are optimized for measurement wavelengths above 550 nm, and small sample amounts, which makes them more compatible with blood samples—although the earlier mentioned drawbacks of these methods have to be taken into account. On the other hand, optimal reading wavelength with best signal-to-noise ratio for simple immunoturbidimetry is below 400 nm.

To enable a working compromise with simple immunoturbidimetry on blood samples the new method is evaluated at approximately 620-650 nm, which is very far from the optimum value of the conventional simple immunoturbidimetry application (e.g. 340 nm). This range is outside the maximum absorption of hemoglobin, but hemoglobin still shows a significant absorption at this wavelength. It was found that in the claimed method this trade-off can be accepted in order to have sufficient signal generated by simple immunoturbidimetry outside its optimum measurement wavelength range.

Also, care has to be taken in the new method to preserve hemoglobin in the oxy-hemoglobin state as most other forms of native or stabilized hemoglobin can have significant absorption even above 600 nm. As a further constraint hemolysis or stabilization of hemoglobin may not block or interfere with the immunoreaction with simple antibodies. In a preferred embodiment, hemolysis has to be almost instantaneous to enable short measurement times, and would not need a dedicated step or separate reagents. It was found that a reaction buffer containing high concentration (>0.5% (w/v)) of non-ionic detergents is suitable to achieve these goals for the new method.

Whole blood samples contain a serum portion determined by the hematocrit value of the sample because of the volume occupied by blood cells. Common clinical chemistry analytes are contained in, and their reference concentrations are determined for serum or plasma. As described in the prior art the variable serum content of whole blood can be taken into account using hematocrit correction calculation (Horiba: U.S. Pat. No. 6,030,845, EP 0 822 412 B1).

The hematocrit value for the present invention can be determined independently from the immunoassay measurement, for example on an integrated blood cell counting apparatus working with a different portion of the same whole blood sample using conventional methods (different from: Quotient: US 2010075338 A1, EP 2 135 075 B1, Horiba: U.S. Pat. No. 8,570,495 B2, EP 2 434 289 B1).

Not only reduced serum content, but also application of a sub-optimal measurement wavelength contributes to a significant signal loss when compared to conventional serum measurements. Compensation of these effects is possible by increasing the sample volume, and thus sample ratio in the final reaction mixture. In the present method, ratio of sample volume in relation to total final volume is >10%. Unfortunately, elevated blood sample ratio can be associated with a significant background absorption dominated by the residual absorption of hemoglobin, which is dependent on the measurement wavelength used. High blood sample ratio in the reaction mixture also often leads to undesired interactions between sample and reagents, and thus produces measurement artifacts which are accounted for by some further aspects of the invention detailed below.

To provide an optimal signal-to-noise ratio clinical chemistry methods are optimized to work under specific environmental conditions. Often different methods are performed on an analyzer working at a single, fixed reaction temperature. Many enzymatic and immunological reactions have a positive temperature coefficient or a temperature optimum in the physiological range. Therefore, a reaction temperature of 37° C. or slightly above is conventionally used for these methods, including routine immunoturbidimetry—and has become a widely used, common practice in the industry.

It was discovered in the described invention that some of the problems of earlier mentioned artifacts on whole blood samples can be solved in the new simple immunoturbidimetry reaction if temperature for the reaction is set lower than the conventionally used 37° C. environment. It was also found that a 22 to 28° C. reaction temperature not only blocks unspecific background processes but despite expectations it also does not compromise specific signal intensity on the experimental setup used.

Further difficulties were identified when using high amounts of complex biological samples (e.g. blood) containing significant amounts of interfering substances, in parallel with low analyte concentrations associated with low signal intensities. Difficulties with non-linear dilution effects and reagent blanking can potentially compromise precise measurements under these circumstances. To counteract these problems a modified signal calculation method was developed and implemented for the present invention.

Conventional end-point methods take a reference absorbance reading before addition of the active reagent and a second reading after incubation with the active reagent. Kinetic or fixed-point methods take two or more absorbance readings after the active reagent is added, in which case the rate of change can be calculated as absorbance change divided by time. The signal is calculated from the change observed between different readings or from the rate of change. According to established prior art the chosen method for signal calculation is determined by the assay to be used, uniformly for different samples.

The new immunoturbidimetry method without particle enhancement and also conventional methods may benefit from an adaptive evaluation, where the signal is calculated as a weighed combination of end-point and fixed-point methodologies. Several readings are taken during the measurement protocol, but their interpretation is made dependent on signal intensity.

Fixed-point calculation eliminates many uncertainties related to dilution artifacts and reagent blanks on low signal samples. On the other hand, it is not suited for high signal samples if a significant portion of total signal is generated before the first absorbance reading after addition of the active reagent. The reason for this is that absorbance immediately after the addition of the active reagent cannot be measured directly due to the finite time required to physically add and mix the reagent. End-point calculation is better suited for these high signal samples. As there is a strong signal in this case the relative contribution of the above-mentioned reagent addition artifacts is significantly lower and their influence on results is marginal.

Weighing between the two methods for signal calculation can be based on different parameters related to signal amplitude of the given sample. A smooth transition of signal calculation between the two extreme cases of very low and very high signal samples can guarantee optimal assay performance over a wide range of analyte concentrations. Although this adaptive calculation becomes necessary because of high background absorbance and artifacts related to whole blood as a sample, the calculation method may also be implemented for other sample types.

The combination of the above characteristics allows not only to use whole blood as a measurement sample, but also measurement time of conventional immunoturbidimetry can be significantly reduced. At the same time the claimed method makes the use of insoluble particles unnecessary. Using a single whole blood sample for both blood cell counting and determination of one or more further biomarkers using immunoturbidimetry without particle enhancement is made possible. This can be used for example on integrated blood cell counting and immunoturbidimetry analyzers for simple, fast and cost-effective assays.

In a further embodiment of the invention not only the change in absorbance is used for signal calculation but also other parameters recorded during the immunoassay are analyzed. Using the correlation between value, imprecision or inaccuracy of results and further absorbance parameters it could be possible to improve results. These additional parameters could include e.g. absorbance value or rate of absorbance change at specific points of the absorbance curve. On an integrated analyzer apart from the hematocrit value any other blood cell counting parameter influencing results could be available for use for such corrections (e.g. RBC, HGB, WBC, PLT).

A modification of the assay would take advantage of different absorbance readings during the hemolysis process. This data can be used to check for the stability or completeness of hemolysis. In normal cases a stabilization of absorbance during hemolysis is expected. In case of incomplete or ongoing hemolysis a prolonged absorbance decrease can be detected. In case of abnormal samples unspecific background processes causing an unexpected decrease or increase during or after hemolysis (which could influence the result of the following specific immunoturbidimetric reaction) can be identified.

A further possible modification of the method involves additional absorbance readings after addition of the active reagent at different positions in time, but before full development of the assay signal. Real-time evaluation of these readings could provide preliminary, although lower reliability results much earlier than the final result. For a point-of-care application it is desirable to have first results as soon as possible. Using the present invention, a qualitative or semi-quantitative result can be available several minutes earlier than the final result, which can help in building a first diagnostic impression. The measurement can be terminated to save time if lower reliability of the preliminary result is accepted or it can be continued until the final result is generated depending on the settings of the analyzer or on the decision of the user.

It is to be noted that published patent application WO 2018/114060 A1 refers regarding an immunoturbidimetric assay always to the use of a particle which aggregates an antibody (comp. claims 2-4). This publication is silent about omitting the particle and does not provide any example for a turbidimetric assay. According to the description the document mentions only the preferred use of CRP (C-reactive protein) bound to a particle, such as a latex bead (comp. page 4, lines 11-13). Thus, WO 2018/114060 A1 does not guide to an immunoturbidimetric assay without particles for aggregating antibodies and is further silent about temperature and wavelength at which an immunoturbidimetric assay has to be performed, which both represent essential features for performing the assay of the present invention and distinguishes it from the prior art.

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

FIG. 1 shows absorption spectra in the 300-700 nm wavelength range. The solid line represents the absorption difference spectrum of a reaction mixture after immune agglutination without particle enhancement versus a reaction blank. It is calculated as a difference between absorption of the reaction mixture with and without the target molecules to be detected. The difference spectrum shows the change in absorbance due to the formation of immune complexes, which is the useful signal of the reaction and which is proportional to the concentration of the targeted analyte. The reaction mixture consists of reaction buffer, serum sample containing CRP as target molecule, and the active reagent with anti-CRP antibodies without insoluble carriers. The agglutination product shows absorption in a wide wavelength range with continuously decreasing absorption at higher wavelengths. A conventional immunoturbidimetric reaction without insoluble carriers is usually read at a wavelength around 340 nm, where the reaction product gives a strong signal (Reading 'A'). The dashed line represents the absorption spectrum of whole blood sample following hemolysis by a reaction buffer containing 2% (w/v) non-ionic detergent. Hemoglobin absorption is very high below 500 nm and it shows a strong drop at around 600 nm.

The present invention takes advantage of using a wavelength little above 600 nm to avoid extreme absorption by hemoglobin (Reading 'B'). Thus strong background absorbance of hemolyzed whole blood samples can be avoided, which could compromise detection linearity of the assay. Hemoglobin exhibits a decreased but still significant absorption at around e.g. 620 nm (Reading 'B'). The simple immunoturbidimetry product signal significantly decreases at longer wavelengths. Therefore the 600-650 nm range can be considered sub-optimal for reading the conventional immunoturbidimetric reaction without insoluble carriers on serum samples. Nevertheless, it was found to be a useful compromise in the present invention for measurements on hemolyzed whole blood samples.

Figure 2:
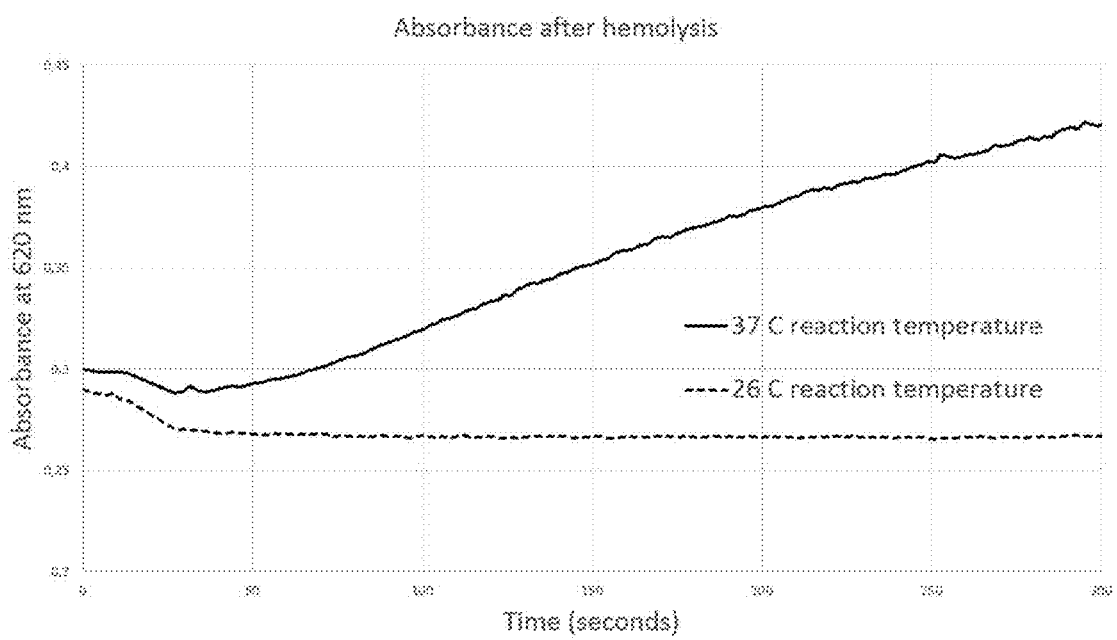
FIG. 2 shows absorbance curves recorded at 620 nm at different temperatures on the same whole blood sample

FIG. 2 shows absorbance curves recorded at 620 nm at different temperatures on the same whole blood sample following hemolysis by a reaction buffer containing 2% (w/v) non-ionic detergent. The solid line represents absorbance at 37° C. reaction temperature. An unspecific absorbance increase artifact can be observed after hemolysis, which could interfere with the specific immunoturbidimetric reaction. The dashed line represents absorbance at 26° C. reaction temperature on the same sample. It is to be noted that absorbance is stabilized after hemolysis.

Figure 3:
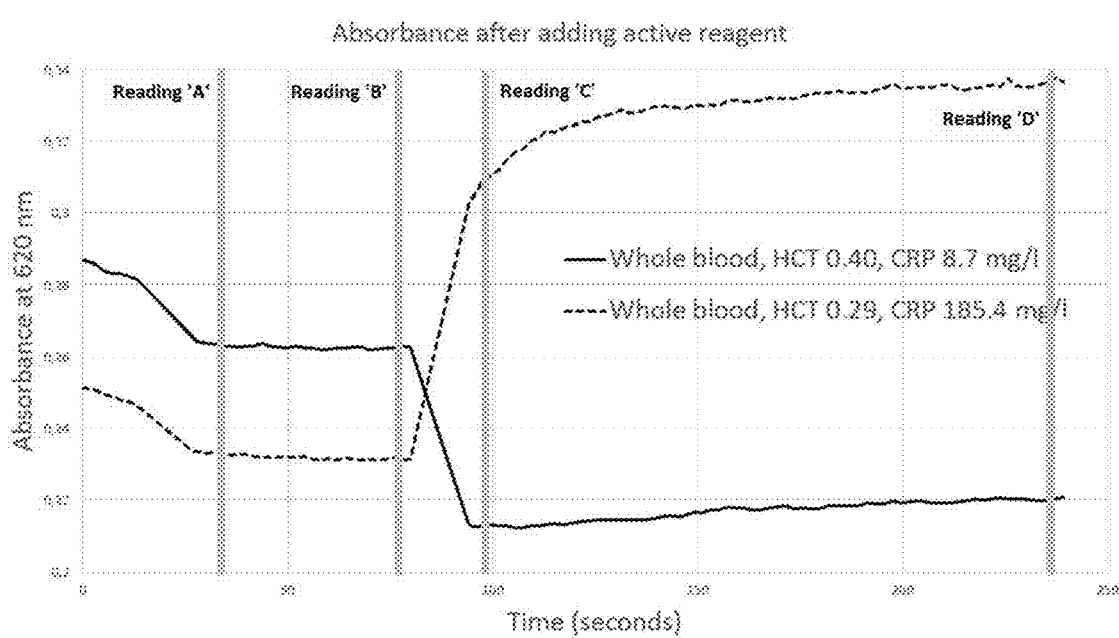
FIG. 3 shows absorbance curves of whole blood samples with different analyte concentrations in a reaction buffer

FIG. 3 shows absorbance curves of whole blood samples with different analyte concentrations in a reaction buffer containing 2% (w/v) non-ionic detergent after addition of the anti-CRP antibody active reagent (at 80 seconds). The suggested absorbance reading points are marked with the letters A-D. The solid line shows a low CRP whole blood sample and the dashed line represents a high CRP whole blood sample.

Conventional end-point methods rely on the absorbance difference between readings 'D' and 'B' in FIG. 3 and are influenced by dilution and reagent blank artifacts during addition of the active reagent. Conventional fixed-point methods rely on the absorbance difference between readings 'D' and 'C' and are free from influence of artifacts during active reagent addition, but a significant portion of total useful signal is lost on high signal samples during the time between addition of the active reagent and reading 'C'. The adaptive signal calculation method is dominated by the fixed point evaluation ('D'-'C') for low signal samples, and by the end-point evaluation ('D'-'B') for high signal samples. One of the possibilities for weighing between the two extreme cases is to use for example the signal generated during addition of the active reagent ('C'-'B').

The difference between readings 'B' and 'A' in FIG. 3 can be used to check for completeness of hemolysis, or for the presence of hemolysis or sample artifacts.

An additional absorbance reading shortly after reading 'C' or real-time monitoring of absorbance can be used to give a first estimation of analyte concentration at an early stage without having to wait for the second part of the reaction to develop. The low reliability preliminary result can be available in a significantly shorter time than the final result.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for measuring an immunoreaction, the method comprising the steps of:
   a. providing a whole blood sample;
   b. Adding a reaction buffer comprising a non-ionic detergent for hemolysis;
   c. incubating a mixture of steps a. and b. in a first temperature range between 22° C. to 28° C.;
   d. measuring an absorbance or measuring scattered light value of the first mixture during a first incubation at a wavelength in a range between 600 to 680 nm;
   e. adding to the first mixture a buffered solution, which is free of any insoluble antibody for carrier, comprising at least one specific antibody binding at least one specific target thereby forming a second mixture;
   f. incubating the second mixture of step e. in a temperature range between 22° C. to 28° C.;
   g. measuring an absorbance or measuring scattered light value of the second mixture during a second incubation at a wavelength in a range between 600 to 680 nm;
   h. Determining a change in absorbance or scattered light values by calculating the difference between the measured absorbances or scattered light values from steps d. and g.

2. The method of claim 1, wherein the absorbance during first and second incubation is measured at a wavelength in a range between 620 to 650 nm.

3. The method of claim 1, wherein the incubation temperature is in a range between 24° C. to 26° C. during first and second incubation.

4. The method of claim 1, wherein a concentration of the non-ionic detergent is above 0.5% (w/v).

5. The method of claim 1, wherein a final reaction mixture comprising the at least one antibody comprises at least 10% (v/v) whole blood sample.

6. The method of claim 1, wherein the absorbance has been determined at least at two points in time prior to adding the buffered solution comprising the at least one antibody to ensure completeness of hemolysis and absence of artifacts by detecting a constant absorbance.

7. The method of claim 1, comprising a step of determining absorbance at least once after adding the buffered solution comprising the at least one antibody.

8. The method of claim 1, wherein the absorbance is determined shortly after addition of the at least one antibody and at a second time at the end of total incubation in step f. in claim 1.

9. The method of claim 1, further comprising determination of values for cell counting.

10. The method of claim 9, wherein a hematocrit value is determined.

11. The method of claim 1, comprising real-time determination of absorbance.

* * * * *